US006642029B1

(12) United States Patent
Valenzuela et al.

(10) Patent No.: US 6,642,029 B1
(45) Date of Patent: Nov. 4, 2003

(54) HYBRID DNA SYNTHESIS OF MATURE INSULIN-LIKE GROWTH FACTORS

(75) Inventors: Pablo D. T. Valenzuela, Santiago (CL); Guy Mullenbach, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/442,800

(22) Filed: May 17, 1995

Related U.S. Application Data

(63) Continuation of application No. 06/922,199, filed on Oct. 23, 1986, now abandoned, which is a continuation of application No. 06/487,950, filed on Apr. 25, 1983, now abandoned.

(51) Int. Cl.$^7$ ............................ C12N 1/19; C12P 21/04; C07K 14/475

(52) U.S. Cl. .................. 435/69.7; 435/69.8; 435/69.9; 435/320.1; 435/325; 435/254.1; 435/254.11; 435/254.21; 530/324; 530/350; 530/399; 536/23.4; 536/23.5

(58) Field of Search ..................... 530/324, 350, 530/399; 435/69.4, 69.7, 69.8, 69.9, 172.3, 240.2, 320.1, 255.1, 252.3, 325, 254.1, 254.11, 254.21; 536/23.4, 23.5

(56) References Cited

U.S. PATENT DOCUMENTS

| | | | |
|---|---|---|---|
| 4,338,397 A | | 7/1982 | Gilbert et al. |
| 4,443,539 A | | 4/1984 | Fraser et al. |
| 4,546,082 A | | 10/1985 | Kurjan et al. |
| 4,745,179 A | * | 5/1988 | Ueda et al. ................. 530/350 |
| 5,084,384 A | * | 1/1992 | Wong et al. ............... 435/69.4 |
| 5,210,028 A | * | 5/1993 | Schmitz et al. ............ 435/69.4 |
| 6,017,731 A | | 1/2000 | Tekamp-Olson et al. |
| RE37,343 E | | 8/2001 | Tekamp-Olson |

FOREIGN PATENT DOCUMENTS

| | | |
|---|---|---|
| EP | 035 384 | 9/1981 |
| EP | 036 259 | 9/1981 |
| EP | 116 201 | 8/1984 |
| EP | 121 352 | 10/1984 |
| EP | 123294 | 10/1984 |
| EP | 123 544 | 10/1984 |
| EP | 128 733 | 12/1984 |
| EP | 135 094 | 3/1985 |
| EP | 193112 | 2/1986 |
| WO | WO 84 03103 | 8/1984 |

OTHER PUBLICATIONS

Hammarberg, B. et al., *J. of Biotechnology*, 14:423–38, 1990.*
Hammarberg, B. et al., *PNAS*, 86:4367–4371, 1989.*
Humbel, R.E., *Eur. J. Biochem.*, 190:445–62, 1990.*
Rinderknecht, E. et al., *J. Biol. Chem.*, 253(8): 2769–2776, 1978.*
Rhee, H.J. et al., *J. of BioTechnology*, 13:293–304, 1990.*
Rinderknecht, E. et al., *FEBS Letters*, 89(2):283–286, 1978.*
Genentech, Inc. v. Chiron Corporation, 112 F.3d 495 (Fed. Cir.1997).
Genentech, Inc. v. Chiron Corporation, 220 F.3d 1345 (Fed. Cir. 2000).
Hinnen et al., "High Expression and Secretion of Foreign Proteins in Yeast," *Gene Expression in Yeast*. Proceedings of the Alko Yeasst Symposium Helsinki 1983, ed. by M. Korhola & E. Vaisanen. Foundation for Biotechnical and Industrial Fermentation Research 1 (1983): 157–163.
Unlisted Drugs, vol. 32, No. 8, Aug. 1980, p. 117.
Bennetzen et al., *J. Biol. Chem.* (1982) 257(6):3026–3031.
*Biotechnology News* (1983) 3(10):1–3.
Davis et al., *Nature* (1980) 283:433–438.
Emr et al., *Proc. of the Natl. Acad. Sci.* (1980) 80:7080–7084.
Hinnen et al., *Chemical Abstracts* (1985) 102 (5):150, abstract No. 40931K.
Hitzeman et al., *Science* (1983) 219:620–625.
Itakura et al., *Science* (1980) 209:1401–1405.
Khorana, *Science* (1979) 203:614–625.
Kurjan et al., *Cell* (1982) 30:933–943.
Kurjan et al., Abstract of Papers presented at the 1981 Cold Spring Harbor Meeting on The Molecular Biology of Yeast (1981):242.
Li et al., *Proc. Natl. Acad. Sci.* (1983) 80:2216–2220.
Massague et al., *J. Biol. Chem.* (1982) 257:5038–5045.
Meyhack et al., *Experientia* (1982) 38:745.
Miller et al., *Drug Development Research* (1981) 1:435–454.
Rhinderknecht et al., *FEBS Letters* (1978) 89:283–286.
Rhinderknecht et al., *J. Biol. Chem.* 253(8):2769–2776.
Roggen–Kamp et al. *Proc. Natl. Acad. Sci. USA* 78:4466–4470.
Talmadge et al., *Proc. Natl. Acad. Sci.* (1980) 77(7):3988–3992.
Tuite et al., *Embo J.* (1982) 1:603–608.

* cited by examiner

Primary Examiner—Marianne P. Allen
(74) Attorney, Agent, or Firm—Roberta L. Robins; Joseph H. Guth; Robert P. Blackburn

(57) ABSTRACT

Methods and compositions are provided for efficient production of human insulin-like growth factor. Synthetic IGF I and IGF II genes are joined to leader and processing signals which provide for expression and secretion of the gene product in yeast. Enhanced yields of the product may then be recovered from the nutrient medium.

Yeast strains *S. cerevisiae* AB103 (pYIGF-I-10/1) and AB103 (pYIGF-II-10/1) were deposited at the American Type Culture Collection on Apr. 23, 1983 and granted Accession Nos. 20673 and 20674, respectively.

45 Claims, No Drawings

HYBRID DNA SYNTHESIS OF MATURE INSULIN-LIKE GROWTH FACTORS

This application is a continuation of application Ser. No. 06/922,199, filed Oct. 23, 1986, now abandoned which is a continuation of application Ser. No. 06/487,950 (now abandoned), filed Apr. 25, 1983, from which applications priority is claimed pursuant to 35 U.S.C. §120.

BACKGROUND OF THE INVENTION

1. Field of the Invention

It is suspected that the somatic growth which follows the administration of growth hormone in vivo is mediated through a family of mitogenic, insulin-like peptides whose serum concentrations are growth hormone dependent. These polypeptides include somatomedin-C, somatomedin-A, and insulin-like growth factors I and II (IGF I and IGF II). IGF I and II can be isolated from human serum and have amino acid sequences which are broadly homologous to that of insulin. At present, only limited quantities of these growth factors may be obtained by separation from human serum. It would thus be of great scientific and clinical interest to be able to produce relatively large quantities of the growth factors by recombinant DNA techniques.

2. Description of the Prior Art

The amino acid sequences for human insulin-like growth factors I and II (IGF I and II) were first determined by Rinderknecht and Humbel (1978) J. Biol. Chem. 253:2769–2776 and Rinderknecht and Humbel (1978) FEBS Letters 89:283–286, respectively. The nature of the IGF receptors is discussed in Massague and Czech (1982) J. Biol. Chem. 257:5038–5045. Kurjan and Herskowitz, Cell (1982) 30:933–934 describe a putative α-factor precursor containing four tandem copies of mature α-factor, describing the sequence and postulating a processing mechanism. Kurjan and Herskowitz, Abstracts of Papers presented at the 1981 Cold Spring Harbor Meeting on The Molecular Biology of Yeast, p. 242, in an Abstract entitled, "A Putative Alpha-Factor Precursor Containing Four Tandem Repeats of Mature Alpha-Factor," describe the sequence encoding for the α-factor and spacers between two of such sequences.

SUMMARY OF THE INVENTION

Methods and compositions are provided for the efficient production of mature human insulin-like growth factor (IGF). In particular, expression of a "pre"-IGF I and "pre"-IGF II in a yeast host facilitates secretion of the polypeptides into the nutrient medium. DNA constructs are generated by joining DNA sequences from diverse sources, including both natural and synthetic sources. The resulting DNA constructs are stably replicated in the yeast and provide efficient, high level production of processed "pre"-polypeptides which may be isolated in high yield from the nutrient medium.

DESCRIPTION OF THE SPECIFIC EMBODIMENTS

DNA sequences capable of expressing human insulin-like growth factors (IGF I and II) are provided. These DNA sequences can be incorporated into vectors, and the resulting plasmids used to transform susceptible hosts. Transformation of a susceptible host with such recombinant plasmids results in expression of the insulin-like growth factor gene and production of the polypeptide product.

In particular, novel DNA constructs are provided for the production of the precursor polypeptides ("pre"-IGF I and "pre"-IGF II) in a yeast host capable of processing said precursor polypeptides and secreting the mature polypeptide product into the nutrient medium. The DNA constructs include a replication system capable of stable maintenance in a yeast host, an efficient promoter, a structural gene including leader and processing signals in reading frame with said structural gene, and a transcriptional terminator sequence downstream from the structural gene. Optionally, other sequences can be provided for transcriptional regulation, amplification of the gene, exogenous regulation of transcription, and the like. By "pre"-IGF I and "pre"-IGF II, it is meant that the DNA sequence encoding for the mature polypeptide is joined to and in reading frame with a leader sequence including processing signals efficiently recognized by the yeast host. Thus, "pre" denotes the inclusion of secretion and processing signals associated with a yeast host and not any processing signals associated with the gene encoding the polypeptide of interest.

In preparing the DNA construct, it is necessary to bring the individual sequences embodying the replication system, promoter, structural gene including leader and processing signals, and terminator together in a predetermined order to assure that they are able to properly function in the resulting plasmid. As described hereinafter, adaptor molecules may be employed to assure the proper orientation and order of the sequences.

The IGF I and IGF II genes which are employed may be chromosomal DNA, cDNA, synthetic DNA, or combinations thereof. The leader and processing signals will normally be derived from naturally occurring DNA sequences in yeast which provide for secretion of a polypeptide. Such polypeptides which are naturally secreted by yeast include α-factor, a-factor, acid phosphatase and the like. The remaining sequences which comprise the construct including the replication system, promoter, and terminator, are well known and described in the literature.

Since the various DNA sequences which are joined to form the DNA construct of the present invention will be derived from diverse sources, it will be convenient to join the sequences by means of connecting or adaptor molecules. In particular, adaptors can be advantageously employed to connect the 3'-end of the coding strand of the leader and processing signal sequence to the 5'-end of the IGF coding strand together with their respective complementary DNA strands. The leader and processing signal sequence may be internally restricted near its 3'-terminus so that it lacks a predetermined number of base pairs of the coding region. An adaptor can then be constructed so that, when joining the leader and processing sequence to the IGF coding strand, the missing base pairs are provided and the IGF coding strand is in the proper reading frame relative to the leader sequence. The synthetic IGF coding region and/or the adaptor at its 3'-end will provide translational stop codons to assure that the C-terminus of the polypeptide is the same as the naturally occurring C-terminus.

The adaptors will have from about 5 to 40 bases, more usually from about 8 to 35 bases, in the coding sequence and may have either cohesive or blunt ends, with cohesive ends being preferred. Desirably, the termini of the adaptor will have cohesive ends associated with different restriction enzymes so that the adaptor will selectively link two different DNA sequences having the appropriate complementary cohesive end.

The subject invention will be illustrated with synthetic fragments coding for IGF I and IGF II joined to the leader and processing signals of yeast α-factor. The yeast α-factor may be restricted with HindIII and SalI. HindIII cleaves in the processing signal of the α-factor precursor, cleaving 3' to the second base in the coding strand of the glu codon, while the HindIII recognition sequence completes the glu codon, encodes for ala and provides the first 5' base of the amino-terminal trp codon of mature α-factor. With reference to the direction of transcription of the α-factor gene, the SalI site is located upstream of the transcriptional terminator.

The synthetic genes coding for IGF will have nucleotide sequences based on the known amino acid sequences of the IGF I and IGF II polypeptides. Preferably, the synthetic sequences will employ codons which are preferentially utilized by the yeast host, e.g., based on the frequency with which the codons are found in the genes coding for the yeast glycolytic enzymes. Conveniently, the synthetic sequence will include cohesive ends rather than blunt ends for insertion into a restriction site in a cloning vehicle. Furthermore, restriction sites will be designed into the synthetic sequences using silent mutations in order to generate fragments which may be annealed into sequences capable of producing IGF I/IGF II hybrid peptide molecules.

In the examples, the synthetic fragments are provided with cohesive ends for EcoRI and inserted into the EcoRI site in pBR328. Usually, the synthetic sequence will include additional restriction sites proximal to each end of the polypeptide coding region. Such interior restriction sites are selected to provide precise excision of the coding region from the cloning vehicle and for joining to adaptors so that the final DNA construct, including the leader and processing signals and coding region, are in proper reading frame, and in proper juxtaposition to a transcription terminator. Preferably, the restriction sites will have the recognition sequence offset from the cleavage site, where cleavage is directed proximal to the coding region and the recognition site is lost. This allows cleavage precisely at each end of the coding region regardless of the nucleotide sequence. HgaI sites are provided in the examples.

In preparing the synthetic gene, overlapping single stranded DNA (ssDNA) fragments are prepared by conventional techniques. Such ssDNA fragments will usually be from about 10 to 40 bases in length. Although considerably longer fragments may be employed, the synthetic yield decreases and it becomes more difficult to assure that the proper sequence has not been inadvertently degraded or altered. After the ssDNA fragments have been synthesized, they are joined under annealing conditions with complementary base pairing assuring the proper order. The ends of the fragments are then ligated, and the resulting synthetic DNA fragment cloned and amplified, usually in a bacterial host such as *E. coli*. As previously indicated, the synthetic structural gene may be provided with cohesive ends complementary to a suitable restriction site in the cloning vehicle of interest and internal recognition sites which allow for precise excision of the coding region. After cloning and amplification of the synthetic sequences, usable quantities of the sequences may be excised, usually at the internal restriction sites on either end of the IGF coding region.

Conveniently, the promoter which is employed may be the promoter associated with the leader and processing sequence. In this manner, a 5'-portable element, which contains both the promoter and the leader sequence in proper spatial relationship for efficient transcription, may be provided. By further including a transcriptional terminator, a "cassette" consisting of promoter/leader—restriction site (s)—terminator is created, where the IGF coding region may be inserted with the aid of adaptors. Usually, such cassettes may be provided by isolating a DNA fragment which includes an intact gene from a yeast host and the upstream and downstream transcriptional regulatory sequences of the gene, where the gene expresses a polypeptide which is secreted by the host.

Alternatively, one may replace the naturally occurring yeast promoter by other promoters which allow for transcriptional regulation. This will require sequencing and/or restriction mapping of the region upstream from the leader sequence to provide for introduction of a different promoter. In some instances, it may be desirable to retain the naturally occurring yeast promoter and provide a second promoter in tandem, either upstream or downstream from the naturally occurring yeast promoter.

A wide variety of promoters are available or can be obtained from yeast genes. Promoters of particular interest include those promoters involved with enzymes in the glycolytic pathway, such as promoters for alcohol dehydrogenase, glyceraldehyde-3-phosphate dehydrogenase, pyruvate kinase, triose phosphate isomerase, phosphoglucoisomerase, phosphofructokinase, etc. By employing these promoters with regulatory sequences, such as enhancers, operators, etc., and using a host having an intact regulatory system, one can regulate the expression of the processed "pre"-IGF. Thus, various small organic molecules, e.g. glucose, may be employed for the regulation of production of the desired polypeptide.

One may also employ temperature-sensitive regulatory mutants which allow for modulation of transcription by varying the temperature. Thus, by growing the cells at the non-permissive temperature, one can grow the cells to high density, before changing the temperature in order to provide for expression of the "pre"-polypeptides for IGF I and IGF II.

Other capabilities may also be introduced into the construct. For example, some genes provide for amplification, where upon stress to the host, not only is the gene which responds to the stress amplified, but also flanking regions. By placing such a gene upstream from the promoter, coding region and the other regulatory signals providing transcriptional control of the "pre"-polypeptide, and stressing the yeast host, plasmids may be obtained which have a plurality of repeating sequences, which sequences include the "pre"-polypeptide gene with its regulatory sequences. Illustrative genes include metallothioneins and dihydrofolate reductase.

The construct may include in addition to the leader sequence fragment, other DNA homologous to the host genome. If it is desired that there be integration of the IGF gene into the chromosome(s), integration can be enhanced by providing for sequences flanking the IGF gene construct which are homologous to host chromosomal DNA.

The replication system which is employed will be recognized by the yeast host. Therefore, it is desirable that the replication system be native to the yeast host. A number of yeast vectors are reported by Botstein et al., *Gene* (1979) 8:17–24. Of particular interest are the YEp plasmids, which contain the 2 μm plasmid replication system. These plasmids are stably maintained at multiple copy number. Alternatively or in addition, one may use a combination of ARS1 and CEN4, to provide for stable maintenance.

After each manipulation, as appropriate, the construct may be cloned so that the desired construct is obtained pure and in sufficient amount for further manipulation. Desirably, a shuttle vector (i.e., containing both a yeast and bacterial origin of replication) may be employed so that cloning can be performed in prokaryotes, particularly *E. coli*.

The plasmids may be introduced into the yeast host by any convenient means, employing yeast host cells or spheroplasts and using calcium precipitated DNA for transformation or liposomes or other conventional techniques. The modified hosts may be selected in accordance with the genetic markers which are usually provided in a vector used to construct the expression plasmid. An auxotrophic host may be employed, where the plasmid has a gene which complements the host and provides prototrophy. Alternatively, resistance to an appropriate biocide, e.g. antibiotic, heavy metal, toxin, or the like, may be included as a marker in the plasmid. Selection may then be achieved by employing a nutrient medium which stresses the parent cells, so as to select for the cells containing the plasmid. The plasmid containing cells may then be grown in an appropriate nutrient medium, and the desired secreted polypeptide isolated in accordance with conventional techniques. The polypeptide may be purified by chromatography, filtration, extraction, etc. Since the polypeptide will be present in mature form in the nutrient medium, one can cycle the nutrient medium, continuously removing the desired polypeptide.

The following examples are offered by way of illustration and not by way of limitation.

EXPERIMENTAL

Nucleotide sequences for human insulin-like growth factors I and II (IGF I and II) comprising preferred yeast codons were devised based on the amino acid sequences reported in Rinderknecht and Humbel (1978) J.Biol.Chem. 253:2769–2776 and Rinderknecht and Humbel (1978) FEBS Letters 89:283–286, respectively. The sequences (with the coding strands shown 5' to 3') are as follows:

The sequences are provided with EcoRI cohesive ends at both ends. Coding for IGF I begins at base 16 of the coding strand and ends at base 225. HgaI restriction sites are located at each end of the IGF I coding region. The HgaI recognition sites (5'-GACGC-3') lie outside of the IGF I coding region, i.e. between the end of the synthetic sequence and the HgaI cleavage site. The IGF II synthetic sequence is similarly constructed with the coding strand beginning at base 16 and terminating at base 219.

A synthetic DNA fragment for IGF I having the sequence just described for IGF I was prepared by synthesizing 20 overlapping ssDNA segments using the phosphoramidite method (see co-pending application, Ser. No. 457,412, filed Jan. 12, 83). The ssDNA sequences were as follows:

| Designation | Sequence |
|---|---|
| A | AATTCGACGCTTATGG |
| B-I-1 | GTCCAGAAACCTTGTGTGGT |
| C-I-2b | GCTGAATTGGTC |
| C-I-2a | GATGCTTTGCAATTCGT |
| D | TTGTGGTGACAGAGGTTTCTACTTC |
| I-3 | AACAAGCCAACCGGTTACGGTTCTTCTTC |
| E-I-4 | TAGAAGAGCTCCACAAACCGGTATCGTT |
| F-I-5 | GACGAATGTTGTTTCAGATCTTGTGACTTG |
| G-I-6 | AGAAGATTGGAAATGTACTGTGCT |
| I-7 | CCATTGAAGCCAGCTAAGTCT |
| H-I-8 | GCTTCAATGCGTCG |
| J-I-9 | GTTTCTGGACCCATAAGCGTCG |
| K-I-10 | AAAGCATCGACCAATTCAGCACCACACAAG |
| L | CTCTGTCACCACAAACGAATTGC |
| M-I-11 | AACCGGTTGGCTTGTTGAAGTAGAAAC |
| I-12 | TGGAGCTCTTCTACAAGAAGAACCGT |
| I-13 | GAAACAACATTCGTCAACGATACCGGTTTG |
| N-I-14 | CCAATCTTCTCAAGTCACAAGATCT |

A DNA sequence for IGF II was similarly synthesized. The following additional ssDNA fragments were prepared.

| Designation | Sequence |
|---|---|
| B-II-1 | CTTACAGACCATCCGAAACCTTGTGTGGT |
| C-II-2 | GGTCAATTGGTCGACACCTTGCAATTCGT |
| II-3 | TCCAGACCAGCTTCCAGAGTTTCT |
| E-II-4 | AGAAGATCCAGACGTATCGTT |
| F-II-5 | GAAGAATGTTGTTTCAGATCTTGTGACTTG |
| G-II-6 | GCTTTGTTGGAAACCTACTGTGCT |
| H-II-7 | ACCCCAGCTAAGTCTGAATGAATGCGTCG |
| J-II-8 | GTTTCGGATGGTCTGTAAGCCATAAGCGTCG |
| K-II-9 | AAGGTGTCGACCAATTCACCACCACACAAG |
| M-II-10 | AAGCTGGTCTGGAGAAGTAGAAAC |
| II-11 | CTGGATCTTCTAGAAACTCTGG |
| II-12 | GAAACAACATTCTTCAACGATACCT |
| N-II-13 | TTCCAACAAAGCCAAGTCACAAGATCT |
| II-14 | AGACTTAGCTGGGGTAGCACAGTAGGT |
| II-15 | AATTCGACGCATTCATTC |

200 pmoles of these ssDNA fragments and fragments A, D and L were joined in a similar manner as above, wherein A and II-15 were not phosphorylated resulting in the following ordering and pairing of segments.

FIG. 2
IGF II ANNEALING AND LIGATION SCHEME

5'  A   B-II-1   C-II-2   D        II-3   E-II-4   F-II-5   G-II-6   H-II-7  3'
                                   +
3'      J-II-8   K-II-9   L   M-II-10   II-11   II-12   N-II-13   II-14   II-15  5'

| Designation | Sequence |
|---|---|
| I-15 | GGCTTCAATGGAGCACAGTACATTT |
| I-16 | AATTCGACGCATTCAAGCAGACTTAGCT |

The ssDNA segments were joined as follows: 50 pmoles of each segment except A and 1–16 were 5'-phosphorylated with T4 polynucleotide kinase. 50 pmoles all segments were then annealed in a single step as an 18 μl pool by cooling from 95° to 25° over 1.5 hrs. Ligation was achieved in a reaction volume of 30 μl containing 1 mM ATP, 10 mM DTT, 100 mM tris-HCl, pH 7.8, 10 mM $MgCl_2$, 1 μg/ml spermidine and T4 ligase. The appropriate double-stranded fragment resulting from the order and pairing of fragments shown in FIG. 1 was purified on a 7% native polyacrylamide electrophoresis gel.

The synthetic DNA sequences were inserted into the EcoRI site of pBR328 to produce plasmids p328IGF I and p328IGF II. After cloning, the IGF coding strands were excised using HgaI.

Synthetic oligonucleotide adaptors were then ligated to the HgaI restriction fragments. For IGF I, the adaptors had the following sequences:

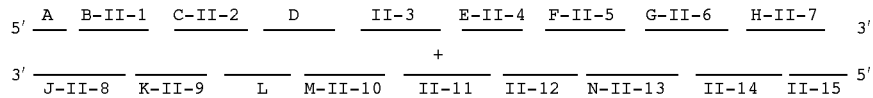

With orientation with respect to the coding strand, the 3'-end of the first adaptor, a), is complementary to the 5' HgaI cleavage site on the IGF I synthetic sequence, while the 5'-end of the first adaptor provides a HindIII cohesive end. The second adaptor, b), is complementary at its 5'-end to the HgaI cleavage site at the 3'-end of the IGF I sequence, while the 3'-end of the adaptor provides a SalI cohesive end.

FIG. 1
IGF I ANNEALING AND LIGATION SCHEME

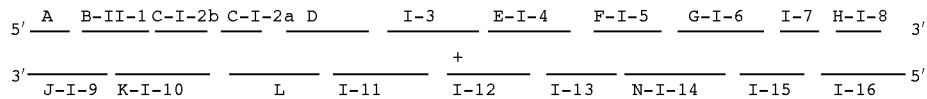

For IGF II, the adaptors had the following sequences:

```
c)   5'-AGCTGAAGCT-3'
         3'-CTTCGACGAAT-5' d)   5'-CTGAATGATAAG-3'
         3'-ACTATTCAGCT-5'
```

With orientation as above the first adaptor, c), is complementary at its 3'-end to the 5'- HgaI cleavage site in the IGF II synthetic sequence, while the 5'-end provides a HindIII cohesive end. The second adaptor, d), is complementary at its 5'-end to the second HgaI cleavage site in the IGF II synthetic sequence and provides a SalI cohesive end at its 3'-end.

The synthetic fragments and adaptors joined thereto were purified by preparative gel electrophoresis and ligated to 100 ng of pAB113 which had been previously digested to completion with endonucleases HindIII and SalI. pAB113 was derived from pAB112 by deletion of the three 63 bp HindIII fragments. pAB112 is a plasmid containing a 1.8 kb EcoRI fragment with the yeast α-factor gene cloned in the EcoRI site of pBR322 in which the HindIII and SalI sites had been deleted. pAB112 was derived from plasmid pAB101 which contains the yeast α-factor gene as a partial Sau3A fragment cloned in the BamHI site of plasmid YEp24. pAB101 was obtained by screening a yeast genomic library cloned in YEp24 using an enzymatically $P^{32}$ radiolabeled synthetic oligonucleotide probe homologous to the published α-factor coding region (Kurjan and Herskowitz, Abstracts 1981 Cold Spring Harbor meeting on the Molecular Biology of Yeasts, page 242).

The resulting mixtures were used to transform *E. coli* HB101 cells, and plasmids pBA113-IGF-I and pAB113-IGF-II were obtained for IGF I and IGF II, respectively.

Plasmids pAB113-IGF-I and pAB113-IGF-II (5 μg each) having the IGF I and IGF II structural genes, respectively, were digested to completion with EcoRI and the resulting fragments were ligated to an excess of EcoRI-BamHI adaptors and digested with BamHI. The resultant 1.8 kb BamHI fragments were isolated by preparative gel electrophoresis and approximately 100 ng of each fragment was ligated to 100 ng of pCl/1, which had been previously digested to completion with BamHI and treated with alkaline phosphatase.

Plasmid pCl/1 is a derivative of pJDB219, Beggs, Nature (1978) 275:104, in which the region corresponding to bacterial plasmid pMB9 in pJDB219 has been replaced by pBR322 in pCl/1. Each ligation mixture was used to transform *E. coli* HB101 cells. Transformants were selected by ampicillin resistance and their plasmids analyzed by restriction endonuclease digestion. DNA from one selected clone for each structural gene, IGF I or IGF II, (pYIGF-I-10/1) or (pYIGF-II-10/1), respectively, was prepared and used to transform yeast AB103 cells. Transformants were selected by their Leu+ phenotype.

Two cultures (5 and 9 liters) of yeast strain AB103 (α,pep 4-3, leu 2-3, leu 2-112, ura 3-52, his 4-580) transformed with plasmid (pYIGF-I-10/1) were grown at 30° C. in-leu medium to saturation (optical density at 650 nm of 5) and left shaking at 30° C. for an additional 12 hr period. Cell supernatants were collected from each culture by centrifugation and the IGF I concentrated by absorption on an ion exchange resin (Biorex-70 available from Bio-Rad Laboratories, Inc., Richmond, Calif.). After elution with 10 mM HCl in 80%, ethanol, the IGF I fractions (0.4 ml and 3 ml, respectively) were assayed for total protein concentration and IGF I concentration. The protein assay was the Coomassie Blue assay available from Bio-Rad Laboratories, Inc., Richmond, Calif. The IGF I assay was a conventional competitive radioimmunoassay employing radiolabeled IGF I. The results were as follows:

| Trial No. | Volume | Volume After Concentration | Total Protein | IGF-I |
|---|---|---|---|---|
| 1 | 5 liters | 0.4 ml | 5.0 mg/ml | 3.75 mg/ml |
| 2 | 9 liters | 3.0 ml | 2.9 mg/ml | 3.00 mg/ml |

A bioassay of IGF I, based on the synergystic effect of the peptide to promote the response of pigeon crop sac to prolactin (Anderson et al. (1983) in Somatomedins/Insulin-Like Growth Factors, Spencer, E. M., ed., Walter deGruter, Berlin) reveals that the IGF I product of these preparations has activity equivalent to authentic IGF I isolated from human serum.

Cultures of AB103(pYIGF-II-10/1) grown similarly to the above and assayed using a human placental membrane radio receptor assay (Spencer et al. (1979) Act. Endocrinol. 91:36–48) for IGF II revealed 3.9 units/ml where normal human serum possesses 1 unit/ml.

In accordance with the subject invention, novel constructs are provided which may be inserted into vectors to provide for expression of human insulin-like growth factor I to provide processing and secretion. Thus, one can obtain a polypeptide having the identical sequence to the naturally occurring human insulin-like growth factor I. By virtue of providing for secretion, greatly enhanced yields can be obtained based on cell population and subsequent preparative operations and purification are simplified.

Although the foregoing invention has been described in some detail by way of illustration and example for purposes of clarity of understanding, it will be obvious that certain changes and modifications may be practiced within the scope of the appended claims.

What is claimed is:

1. A method for producing mature, human insulin-like growth factor-I (IGF-I) in yeast cells, said method comprising growing yeast cells comprising a vector that comprises a DNA sequence, said DNA sequence encoding said IGF-I directly joined in proper reading frame with Saccharomyces α-factor secretory leader and processing signal sequences recognized by said yeast cells downstream from and under the transcriptional regulatory control of a transcriptional initiation region compatible with said yeast cells, wherein said yeast cells are grown under conditions that provide for the production and secretion of said mature, human IGF-I, and isolating said mature, human IGF-I.

2. A method as in claim 1, wherein the DNA sequence encoding human IGF-I is a synthetic sequence having codons preferentially utilized by the yeast cell.

3. A method as in claim 1, wherein the human IGF-I DNA sequence is a synthetic sequence having the following nucleotide sequence:

GlyProGluThrLeuCysGlyAlaGluLeuValAspAlaLeuGln
5'-GGTCCAGAAACCTTGTGTGGTGCTGAATTG
GTCGATGCTTTGCAA CCAGGTCTTTGGAACA
CACCACGACTTAACCAGCTACGAAACGTT
PheValCysGlyAspArgGlyPheTyr-
PheAsnLysProThrGlyTyrGlySerSerSer TTCGTTTGTGGT
GACAGAGGTTTCTACTTCAACAAGCCAACCGGTTA
CGGTTCTTCTTCTAAGCAAACACCACTGTCTCCAA
AGATGAAGTTGTTCGGTTGGCCAATGCCAAGAAGA
AGA

ArgArgAlaProGlnThrGlyIleValAspGluCysCysPheArgSer
CysAspLeuArg AGAAGAGCTCCACAAACCGGTAT
CGTTGACGAATGTTGTTTCAGATCTTGTGAC
TTGAGATCTTCTCGAGGTGTTTGGCCATAGCAA
CTGCTTACAACAAAGTCTAGAACACTGAACTCT
ArgLeuGluMetTyrCysAlaProLeuLysProAlaLysSerAla
AGATTGGAAATGTACTGTGCTCCATTGAAGCCAGC
TAAGTCTGCT-3' TCTAACCTTTACATGACACGAGGT
AACTTCGGTCGATTCAGACGA.

4. The method of claim 3, wherein the yeast cells are Saccharomyces cells.

5. A method as in claim 1, wherein the vector comprises the 2 μm plasmid replication system.

6. The method of claim 1, wherein the yeast cells are Saccharomyces cells.

7. Purified mature, human insulin-like growth factor-I (IGF-I) devoid of other human proteins produced by the process comprising: culturing at least one yeast cell that comprises a vector comprising a DNA construct that encodes said IGF-I directly joined in proper reading frame with Saccharomyces α-factor secretory leader and processing signal sequences recognized by the yeast cell, wherein said culturing is performed under conditions that provide for the production of mature, human IGF-I; and purifying said mature, human IGF-I.

8. Purified mature, human IGF-I protein according to claim 7, wherein the yeast cell is a Saccharomyces cell.

9. A method for producing mature, human insulin-like growth factor-I (IGF-I) in yeast, said method comprising:
  preparing a first DNA fragment comprising a first DNA sequence encoding all or a portion of human IGF-I;
  preparing a second DNA fragment comprising a second DNA sequence encoding all or a portion of Saccharomyces α-factor secretion and processing sequences;
  joining said first and second DNA fragments by means of an adaptor to provide a third DNA fragment, wherein said third DNA fragment comprises the coding sequence for human IGF-I directly joined to Saccharomyces α-factor secretion and processing sequences;
  incorporating said third DNA fragment into an expression vector;
  transforming a yeast cell with said expression vector; and
  culturing said yeast cell under conditions that provide for production of mature, human IGF-I.

10. A method according to claim 9, wherein said expression vector includes a replication system recognized by bacteria.

11. A method according to claim 9, wherein said expression vector comprises the 2 μm plasmid replication system or portion thereof.

12. The method of claim 9, wherein the DNA sequence encoding IGF-I is a synthetic sequence having codons preferentially utilized by the yeast cell.

13. A method as in claim 9, wherein the DNA sequence encoding IGF-I is a synthetic sequence having the following nucleotide sequence:
  GlyProGluThrLeuCysGlyAlaGluLeuValAspAlaLeuGln
    5'-GGTCCAGAAACCTTGTGTGGTGCTGAATTG
    GTCGATGCTTTGCAACCAGGTCTTTGGAACA
    CACCACGACTTAACCAGCTACGAAACGTT
  PheValCysGlyAspArgGlyPheTyrPheAsnLysProThrGly
  TyrGlySerSerSer TTCGTTTGTGGTGACAGAG-
  GTTTCTA CTTCAACAAGCCAACCGGTTACGGTTCT-
  TCTTCT AAGCAAACACCACTGTCTCCAAAGAT-
  GAAGTTGTTCGGTTGGCCAATGCCAAGAAGAAGA
  ArgArgAlaProGlnThrGlyIleValAspGluCysCysPheArgSer
  CysAspLeuArg AGAAGAGCTCCACAAACCGG-
  TATCGTTGACGAATGTTGTTTCAGATCT-
  TGTGACTTGAGA TCTTCTCGAGGTGTTTGGCCAT-
  AGCAACTGCTTACAACAAAGTCTAGAACACTGAA
  CTCT
  ArgLeuGluMetTyrCysAlaProLeuLysProAlaLysSerAla
  AGATTGGAAATGTACTGTGCTCCATTGAAGCCAGC
  TAAGTCTGCT-3' TCTAACCTTTACATGACACGAGG-
  TAACTTCGGTCGATTCAGACGA.

14. The method of claim 13, wherein the yeast cell is a Saccharomyces cell.

15. The method of claim 9, wherein the yeast cell is a Saccharomyces cell.

16. A DNA construct comprising a sequence coding for human insulin-like growth factor-I (IGF-I) directly joined in proper reading frame with Saccharomyces α-factor secretory leader and processing signal sequences, wherein said DNA construct is capable of providing expression of mature,: human IGF-I.

17. A DNA construct comprising a synthetic coding sequence employing preferred yeast codons for human insulin-like growth factor-I (IGF-I) directly joined in proper reading frame with Saccharomyces α-factor secretory leader and processing signal sequences wherein said coding sequence is downstream from and under transcriptional regulation of regulatory signals utilized by yeast, and capable of providing expression of mature, human IGF-I in yeast.

18. A DNA construct according to claim 17, including a replication system recognized by Saccharomyces.

19. A DNA construct according to claim 18, wherein said yeast replication system comprises the 2 μm plasmid replication system or portion thereof.

20. A DNA construct according to claim 17, wherein said construct includes a replication system utilized by bacteria.

21. A DNA construct according to claim 17, wherein said DNA sequence encoding human IGF-I consists of the sequence:
  GlyProGluThrLeuCysGlyAlaGluLeuValAspAlaLeuGln
    5'-GGTCCAGAAACCTTGTGTGGTGCTGAATTG
    GTCGATGCTTTGCAA CCAGGTCTTTGGAACA-
    CACCACGACTTAACCAGCTACGAAACGTT
  PheValCysGlyAspArgGlyPheTyr-
  PheAsnLysProThrGlyTyrGlySerSerSer TTCGTTTGTG-
  GTGACAGAGGTTTCTACTTCAACAAGC-
  CAACCGGTTACGGTTCTTCTTCT
  AAGCAAACACCACTGTCTCCAAAGAT-
  GAAGTTGTTCGGTTGGCCAATGCCAAGAAGAAGA
  ArgArgAlaProGlnThrGlyIl-
  eValAspGluCysCysPheArgSerCysAspLeuArg AGAA-
  GAGCTCCACAAACCGGTATCGTTGAC-
  GAATGTTGTTTCAGATCTTGTGACTTGAGA
  TCTTCTCGAGGTGTTTGGCCATAG-
  CAACTGCTTACAACAAAGTCTAGAA-
  CACTGAACTCT
  ArgLeuGluMetTyrCysAlaProLeuLysProAlaLysSerAla
  AGATTGGAAATGTACTGTGCTCCATTGAAGCCAGC
  TAAGTCTGCT-3' TCTAACCTTTACATGACACGAGG-
  TAACTTCGGTCGATTCAGACGA.

22. A fusion protein comprising the amino acid sequence of human IGF-I and a yeast α-factor secretory leader and signal sequence.

23. A DNA molecule comprising the nucleotide sequence:
  GlyProGluThrLeuCysGlyAlaGluLeuValAspAlaLeuGln
    5'-GGTCCAGAAACCTTGTGTGGTGCTGAATTG
    GTCGATGCTTTGCAA CCAGGTCTTTGGAACA-
    CACCACGACTTAACCAGCTACGAAACGTT
  PheValCysGlyAspArgGlyPheTyr-
  PheAsnLysProThrGlyTyrGlySerSerSer TTCGTTTGTG- GTGACAGAGGTTTCTACTTCAACAAGC-
CAACCGGTTACGGTTCTTCTTCT
AAGCAAACACCACTGTCTCCAAAGAT-
GAAGTTGTTCGGTTGGCCAATGCCAAGAAGAAGA
ArgArgAlaProGlnThrGlyIl-
eValAspGluCysCysPheArgSerCysAspLeuArg AGAA-
GAGCTCCACAAACCGGTATCGTTGAC-
GAATGTTGTTTCAGATCTTGTGACTTGAGA
TCTTCTCGAGGTGTTTGGCCATAG-
CAACTGCTTACAACAAAGTCTAGAA-
CACTGAACTCT
ArgLeuGluMetTyrCysAlaProLeuLysProAlaLysSerAla
AGATTGGAAATGTACTGTGCTCCATTGAAGCCAGC
TAAGTCTGCT-3' TCTAACCTTTACATGACACGAGG-
TAACTTCGGTCGATTCAGACGA.

24. A method for producing human insulin-like growth factor-I (IGF-I) in yeast cells, said method comprising growing yeast cells comprising a vector that comprises a DNA sequence, said DNA sequence encoding said IGF-I joined in proper reading frame with Saccharomyces α-factor secretary leader and processing signal sequences recognized by said yeast cells and downstream from and under the transcriptional regulatory control of a transcriptional initiation region compatible with said yeast cells, wherein said yeast cells are grown under conditions that provide for the production and secretion of human IGF-I, and isolating human IGF-I.

25. A method as in claim 24, wherein the DNA sequence encoding IGF-I is a synthetic sequence having codons preferentially utilized by the yeast cells.

26. A method as in claim 24, wherein the DNA sequence encoding human IGF-I is a synthetic sequence having the following nucleotide sequence:

GlyProGluThrLeuCysGlyAlaGluLeuValAspAlaLeuGln
5'-GGTCCAGAAACCTTGTGTGGTGCTGAATTG
GTCGATGCTTTGCAA CCAGGTCTTTGGAACA-
CACCACGACTTAACCAGCTACGAAACGTT
PheValCysGlyAspArgGlyPheTyr-
PheAsnLysProThrGlyTyrGlySerSerSer TTCGTTTGTG-
GTGACAGAGGTTTCTACTTCAACAAGC-
CAACCGGTTACGGTTCTTCTTCT
AAGCAAACACCACTGTCTCCAAAGAT-
GAAGTTGTTCGGTTGGCCAATGCCAAGAAGAAGA
ArgArgAlaProGlnThrGlyIl-
eValAspGluCysCysPheArgSerCysAspLeuArg AGAA-
GAGCTCCACAAACCGGTATCGTTGAC-
GAATGTTGTTTCAGATCTTGTGACTTGAGA
TCTTCTCGAGGTGTTTGGCCATAG-
CAACTGCTTACAACAAAGTCTAGAA-
CACTGAACTCT
ArgLeuGluMetTyrCysAlaProLeuLysProAlaLysSerAla
AGATTGGAAATGTACTGTGCTCCATTGAAGCCAGC
TAAGTCTGCT-3' TCTAACCTTTACATGACACGAGG-
TAACTTCGGTCGATTCAGACGA.

27. The method of claim 26, wherein the yeast cells are Saccharomyces cells.

28. A method as in claim 24, wherein the vector comprises the 2 μm plasmid replication system.

29. The method of claim 24, wherein the yeast cells are Saccharomyces cells.

30. A method for producing human insulin-like growth factor-I (IGF-I) in yeast, said method comprising:
preparing a first DNA fragment comprising a first DNA sequence encoding all or a portion of IGF-I;
preparing a second DNA fragment comprising a second DNA sequence encoding all or a portion of Saccharomyces α-factor secretion and processing sequences;
joining said first and second DNA fragments by means of an adaptor to provide a third DNA fragment, wherein said third DNA fragment comprises the coding sequence for human IGF-I joined to Saccharomyces α-factor secretion and processing sequences;
incorporating said third DNA fragment into an expression vector; transforming a yeast cell with said expression vector; and
culturing said yeast cell under conditions that provide for production of human IGF-I.

31. A method according to claim 30, wherein said expression vector includes a replication system recognized by bacteria.

32. A method according to claim 30, wherein said expression vector comprises the 2 μm plasmid replication system or portion thereof.

33. The method of claim 30, wherein the DNA sequence encoding IGF-I is a synthetic gene having codons preferentially utilized by the yeast cell.

34. The method of claim 30, wherein the DNA sequence encoding IGF-I is a synthetic gene having the following nucleotide sequence:

GlyProGluThrLeuCysGlyAlaGluLeuValAspAlaLeuGln
5'-GGTCCAGAAACCTTGTGTGGTGCTGAATTG
GTCGATGCTTTGCAA CCAGGTCTTTGGAACA-
CACCACGACTTAACCAGCTACGAAACGTT
PheValCysGlyAspArgGlyPheTyr-
PheAsnLysProThrGlyTyrGlySerSerSer TTCGTTTGTG-
GTGACAGAGGTTTCTACTTCAACAAGC-
CAACCGGTTACGGTTCTTCTTCT
AAGCAAACACCACTGTCTCCAAAGAT-
GAAGTTGTTCGGTTGGCCAATGCCAAGAAGAAGA
ArgArgAlaProGlnThrGlyIl-
eValAspGluCysCysPheArgSerCysAspLeuArg AGAA-
GAGCTCCACAAACCGGTATCGTTGAC-
GAATGTTGTTTCAGATCTTGTGACTTGAGA
TCTTCTCGAGGTGTTTGGCCATAG-
CAACTGCTTACAACAAAGTCTAGAA-
CACTGAACTCT
ArgLeuGluMetTyrCysAlaProLeuLysProAlaLysSerAla
AGATTGGAAATGTACTGTGCTCCATTGAAGCCAGC
TAAGTCTGCT-3' TCTAACCTTTACATGACACGAGG-
TAACTTCGGTCGATTCAGACGA.

35. The method of claim 34, wherein the yeast cell is a Saccharomyces cell.

36. The method of claim 30, wherein the yeast cell is a Saccharomyces cell.

37. A DNA construct comprising a synthetic coding sequence employing preferred yeast codons for human insulin-like growth factor-I (IGF-I) joined in proper reading frame with Saccharomyces α-factor secretory leader and processing signal sequences, wherein said coding sequence is downstream from and under transcriptional regulation of regulatory signals utilized by yeast, and capable of providing expression in yeast.

38. A DNA construct according to claim 37, including a replication system recognized by Saccharomyces.

39. A DNA construct according to claim 38, wherein said yeast replication system comprises the 2 μm plasmid replication system or portion thereof.

40. A DNA construct according to claim 37, wherein said construct includes a replication system utilized by bacteria.

41. A DNA construct according to claim 37 comprising the sequence:

GlyProGluThrLeuCysGlyAlaGluLeuValAspAlaLeuGln
5'-GGTCCAGAAACCTTGTGTGGTGCTGAATTG
GTCGATGCTTTGCAA CCAGGTCTTTGGAACA-
CACCACGACTTAACCAGCTACGAAACGTT

PheValCysGlyAspArgGlyPheTyrPheAsnLysProThrGlyTyrGlySerSerSer
TTCGTTTGTGGTGACAGAGGTTTCTACTTCAACAAGCCAACCGGTTACGGTTCTTCTTCT
AAGCAAACACCACTGTCTCCAAAGATGAAGTTGTTCGGTTGGCCAATGCCAAGAAGAAGA
ArgArgAlaProGlnThrGlyIleValAspGluCysCysPheArgSerCysAspLeuArg AGAAGAGCTCCACAAACCGGTATCGTTGACGAATGTTGTTTCAGATCTTGTGACTTGAGA
TCTTCTCGAGGTGTTTGGCCATAGCAACTGCTTACAACAAAGTCTAGAACACTGAACTCT
ArgLeuGluMetTyrCysAlaProLeuLysProAlaLysSerAla AGATTGGAAATGTACTGTGCTCCATTGAAGCCAGCTAAGTCTGCT-3'
TCTAACCTTTACATGACACGAGGTAACTTCGGTCGATTCAGACGA.

42. A DNA construct according to claim 41, wherein the yeast is Saccharomyces.

43. A DNA construct according to claim 37, wherein the yeast is Saccharomyces.

44. A DNA construct comprising a sequence coding for human insulin-like growth-factor I joined in proper reading frame with Saccharomyces α-factor secretory leader and processing signal sequences.

45. A fusion protein comprising the amino acid sequence of IGF-I and Saccharomyces alpha-factor secretory leader and signal sequences.

* * * * *